United States Patent
Choquet

(10) Patent No.: US 6,877,674 B2
(45) Date of Patent: Apr. 12, 2005

(54) PERFUME DIFFUSER

(75) Inventor: Alain Choquet, Harnes (FR)

(73) Assignee: Visteon Global Technologies, Inc., Van Buren Township, MI (US)

( * ) Notice: Subject to any disclaimer, the term of this patent is extended or adjusted under 35 U.S.C. 154(b) by 286 days.

(21) Appl. No.: 09/947,672

(22) Filed: Sep. 6, 2001

(65) Prior Publication Data

US 2002/0074421 A1 Jun. 20, 2002

(30) Foreign Application Priority Data

Sep. 6, 2000 (FR) .............................. 00 11376

(51) Int. Cl.$^7$ .............................................. A24F 25/00
(52) U.S. Cl. .............................. 239/58; 239/59; 239/60; 239/34; 239/37; 239/57
(58) Field of Search .............................. 239/58, 59, 60, 239/34, 37, 39, 41, 42, 43, 47, 51.5, 53, 54, 55, 56, 57

(56) References Cited

U.S. PATENT DOCUMENTS

| | | | | |
|---|---|---|---|---|
| 4,523,870 A | * | 6/1985 | Spector | 454/157 |
| 4,903,584 A | * | 2/1990 | Styles | 454/284 |
| 5,115,975 A | * | 5/1992 | Shilling | 239/55 |
| 5,147,582 A | * | 9/1992 | Holzner et al. | 261/30 |
| 5,242,111 A | * | 9/1993 | Nakoneczny et al. | 239/47 |
| 5,342,584 A | * | 8/1994 | Fritz et al. | 422/124 |
| 5,762,549 A | * | 6/1998 | Scheuer et al. | 454/157 |
| 6,123,906 A | * | 9/2000 | Farmer | 422/124 |

* cited by examiner

Primary Examiner—Davis Hwu
(74) Attorney, Agent, or Firm—Brinks Hofer Gilson & Lione

(57) ABSTRACT

The invention relates to a fitting for a motor vehicle, in particular a dashboard. The permitting the circulation of at least one stream of air, along a given path, behind at least one thickness of material defining a face of the fitting. The fitting further includes means for diffusing an active compound into the at least one stream of air. The diffusing means are capable of being introduced, wholly or in part, through at least one orifice, or passing through the thicknesses of material. The loading orifices being orientated transversely to the path of the stream. The diffusing means are held in the area of the thickness or thicknesses of material.

18 Claims, 2 Drawing Sheets

PERFUME DIFFUSER

RELATED APPLICATION

The present application claims priority of French patent application No. FR 0011376 filed Sep. 6, 2000.

TECHNICAL FIELD OF THE INVENTION

The invention relates to a fitting for a motor vehicle. In particular the invention relates to a perfume diffuser installed in a dashboard of a motor vehicle.

BACKGROUND OF THE INVENTION

Currently, to enable perfume to be diffused inside a motor vehicle, use is typically made of diffusers suspended in the passenger compartment, for example, in the area inside the rear-view mirror or a diffuser added to the driving position.

It has also been suggested placing a perfume diffuser into the inlet of the ventilating, heating and air conditioning device of the vehicle. Typically, such diffusers are located under the cover panel of the dashboard, thus satisfying aesthetic and safety requirements.

However, the above solution has drawbacks, since the diffuser is located in an area to which it is difficult to gain access, which makes it complicated to install. In the same way, the dashboard has to be removed in order to withdraw or change it. Furthermore, the perfume diffused through the passenger compartment is the same everywhere.

BRIEF SUMMARY OF THE INVENTION

The object of the present invention is to provide a fitting for a motor vehicle, in particular a dashboard, that overcomes the aforementioned drawbacks and makes available means for diffusing an active compound such as, for example, a perfume, which can be satisfactorily held in place while, at the same time, being easily accessible.

Another object of the present invention is to provide a fitting for a motor vehicle, in particular a dashboard, which makes available means for diffusing an active component such as, for example, a perfume, and which can be easily removed and/or changed.

Another object of the present invention is to provide a fitting for a motor vehicle, in particular a dashboard, which makes available means for diffusing an active component such as, for example, a perfume, allowing the diffusion of active ingredients that differ according to the area of the passenger compartment in question.

The invention relates to a fitting for a motor vehicle, in particular a dashboard, permitting the circulation of at least one stream of air, along a given path, behind at least one thickness of material defining a face of the fitting. The fitting is designed to be at least temporarily accessible. The fitting includes a diffusing means for diffusing an active compound in the stream characterized by the fact that the diffusing means are designed to be capable of being introduced, wholly or in part, through at least one orifice passing through the thicknesses of material, from the outer face and emerging in the stream. The loading orifice is preferably orientated transversely to the path of the stream. The diffusing means being also capable of being held in the area of the thicknesses of material.

Further objects, features and advantages of the invention will become apparent from consideration of the following description and the appended claims when taken in connection with the accompanying drawings.

DETAILED DESCRIPTION OF THE PREFERRED EMBODIMENTS

Figure 1:
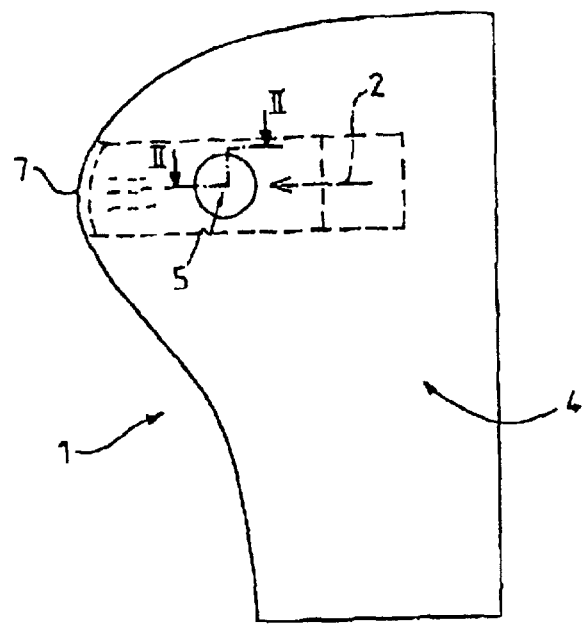
FIG. 1 is a side view of an exemplary embodiment of the fitting according to the invention.
Figure 2:
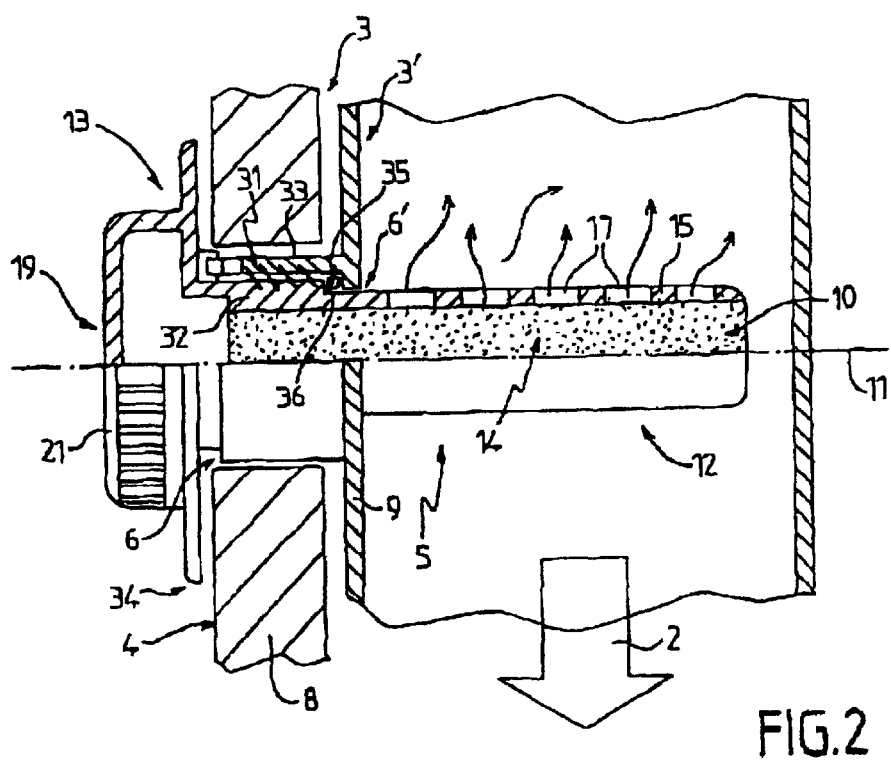
FIG. 2 is a cross-sectional view along line II—II shown in accordance to FIG. 1.
Figure 4:
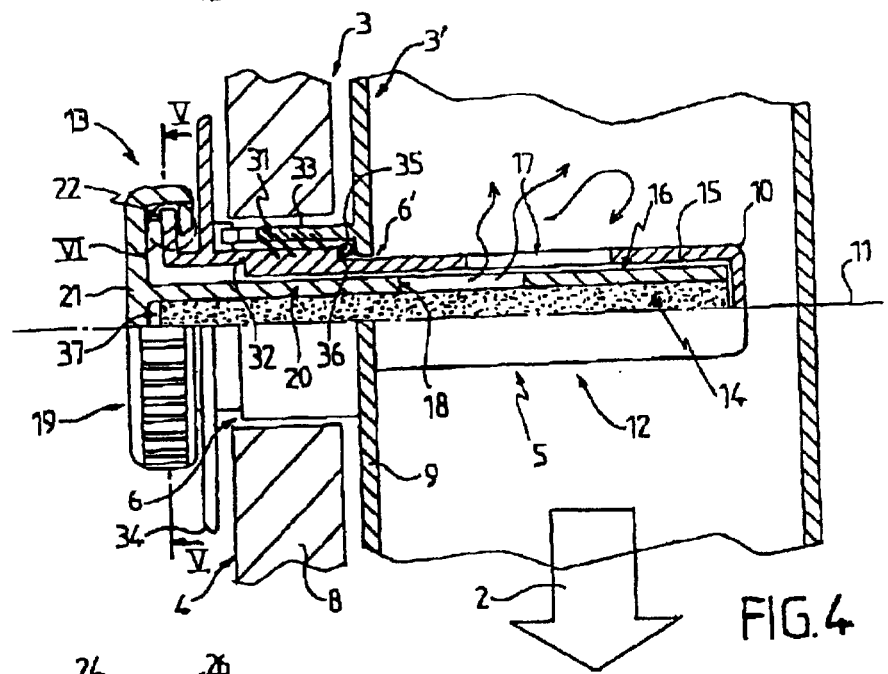
FIG. 4 illustrates, along the same section line as used for FIG. 2, an alternative embodiment of the invention.

As illustrated in FIGS. 1, 2 and 4, fitting 1 according to the invention allows circulation of at least one stream of air, along a given path 2. The fitting defines at least one thickness of material 3, 3'. The thickness of the material 3,3' define a face 4 of fitting 1 (as shown in FIG. 1). The face 4 is also called outer face throughout the application and is adaptable to be temporarily accessible.

In this application, the term "temporarily accessible" means that the outer face 4 is visible without having to remove all or part of fitting 1. For example, the outer face 4 may be the front, as illustrated in FIG. 1 on the lateral faces of the instrument panel.

Fitting 1, also includes diffusing means 5 for diffusing an active compound, in particular a perfuming agent, in the stream of air along a given path 2.

According to the invention, the diffusing means 5 are designed to be capable of being introduced, wholly or in part, through at least one loading orifice 6, 6'. In addition, the diffusing means 5 are capable of passing through the thicknesses of material 3, 3'. Preferably, the orifices 6, 6' are orientated transversely to path 2. The diffusing means 5 is held in place and prevented from displacement by holding the diffusing means 5 in an area of the thicknesses of material 3, 3'.

Therefore, in accordance with the teachings of the preferred embodiment, an active compound can be diffused in a stream of air with diffusing means 5. Further, the installation of the diffusing means 5 is easier as it is carried out via the outside of the fitting 1 without removing the fitting. Further, the diffusing means 5 are reliably held in place.

It is further possible to diffuse different active components through the passenger compartment by providing diffusing means 5 having a different active compound for each air stream.

According, one preferred embodiment of the present invention, diffusing means 5 are capable of being removed in relation to the rest of fitting 1. Therefore, the diffusing means 5 can be removed or changed, when the active compound has been used up.

As shown in FIG. 7, the diffusing means 5 are located, in particular, just upstream of ventilation orifices 7, provided on the front face 4 of said fitting 1 and in the area in which the streams of air emerge.

The fitting 1 can further include ventilating, heating and/or air conditioning system (HVAC). Preferably, the HVAC system located upstream of the diffusing means 5.

As illustrated in FIG. 1, the fitting 1 comprises an instrument panel capable of permitting the circulation of one of the air streams in the direction of each of its lateral ends. In the vicinity of the lateral ends are located at least some of the ventilation orifices 7. The instrument panel is then provided with the diffusing means 5 in the area of one of its lateral faces, designed to be located opposite the front doors of the vehicle. Therefore, the diffusing means 5, while remaining accessible, is concealed when the doors of the vehicle are closed.

Referring in particular to FIG. 1, the fitting 1 includes, in particular, a panel 8 defining the outer face 4 and at least one flow conduit 9 for the air stream. As shown, the conduit 9 is provided behind the panel 8. The loading orifices 6, 6' comprises a first port 6, provided in the panel 8, and a second port 6', provided in conduit 9. The first port 6 and the second form the loading orifices 6, 6'. The first port 6 and the second port 6' are placed in axial prolongation of one another.

The diffusing means 5 comprises a cartridge 10 extending in at least one direction 11, or so-called axial direction. The cartridge 10 is capable of being positioned, over a portion of its diffusing length 12, or so as to extend to meet the air stream. Preferably, the air stream passes through the diffusing length 12 and over a fixing portion 13, at least partially in the loading orifice 6, 6'. When the cartridge 10 is in place, the axial direction 11 and the axis of the loading orifice 6, 6', may possibly coincide.

Figure 3:
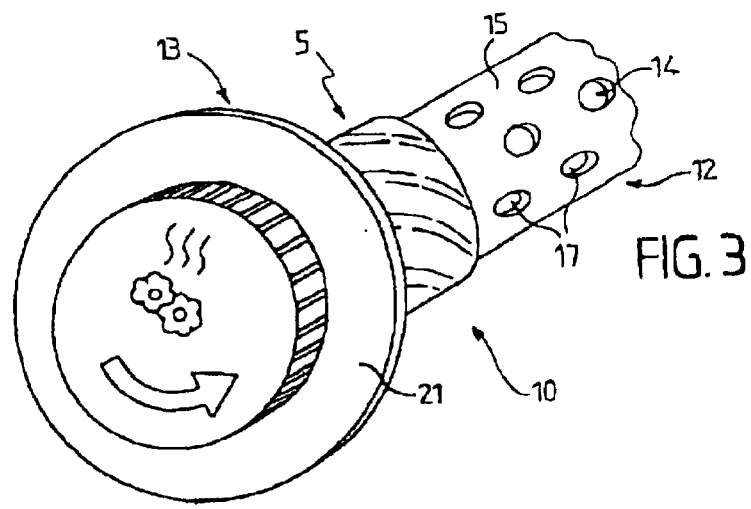
FIG. 3 is a perspective view illustrating one of the constituent elements of the fitting shown in FIG. 2.

As illustrated in FIGS. 2 to 4, the cartridge 10 comprises in the diffusing length 12, a support means 14 for the active compound. Preferably, the active compound is designed to be volatile, and can penetrate through the permeable enclosure 15 covering the support means 14.

The permeable enclosure 15 is formed of a reservoir made of a porous material such as ceramic, foam, paper or the like. Further, the permeable enclosure 15 is capable of containing or absorbing by capillary effect several millimeters of liquid or other active substance.

Referring in particular to FIG. 4, the fitting 1 can further include means 16 for causing the permeability of the enclosure 15 to vary. Preferably, the permeable means 16 has a passage surface 17 for the passage of the vapours of the active compound. The means 16 for causing permeability of the enclosure 15 to vary comprises, a closing surface 18, mobile between the support means 14 and the enclosure 15. The aperture of the passage surface 17 and, the movements of the closing surface 18 are controllable from the end of the cartridge located in the area of the fixing portion 13, at the outer end 19. Therefore, permeability of the enclosure 15 can be adjusted without removing either the fitting 1 or the cartridge 10.

For this purpose, the enclosure 15 and the closing surface 18 comprise two associated enclosures, co-operating with one another in translation and/or rotation.

With regard to translation co-operation, the enclosure 15 and the closing surface 18 have, for example, the same polygonal profile, in particular a square one, and the closing surface 18 is capable of sliding through the enclosure 15 along their common longitudinal axis.

With regard to rotation co-operation, the enclosure 15 and the closing surface 18 comprise two coaxial cylinders. The closing surface 18 is preferably mobile about its longitudinal axis and has an axial prolongation 20 along the fixing portion 13. The axial prolongation 20 defines the outer end 19 of cartridge 10. The axial prolongation 20 comprises an adjusting thumb wheel 21 that enables the closing surface 18 to be rotated.

Figure 5:
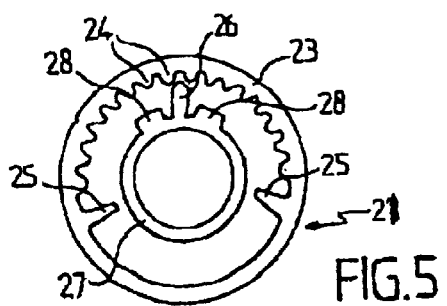
FIG. 5 is a cross-sectional view along line V—V as shown in FIG. 4.

As illustrated in FIG. 5, the cartridge 10 may be provided with indexing means 22. The indexing means 22 helps locate the relative position of the closing surface 18 and the enclosure 15. The indexing means 22 preferably comprises a mobile portion, provided in the area of the thumb wheel 21, and a fixed portion of the fitting 1.

Preferably, the thumb wheel 21 has an annular body 23 provided with internal teeth 24 and stops 25. The teeth 24 co-operate with an index pin 26, mounted at a fixed point on fitting 1, for example, in the area of an index ring 27. The index ring 27 is also equipped with stops 28.

The cooperation between the internal teeth 24 and a pin 26, alters the permeability of the enclosure 15. The function of the stops 25, 28 of thumb wheel 21 and of index ring 27 will be explained in greater detail hereinafter.

The closing surface 18 defines a housing 37 for the support means 14. It is further designed to be mobile in relation to the enclosure 15 in translation along their common longitudinal axis. Therefore, the support means 14 can be changed without changing the entire cartridge 10.

The indexing means 22 are thus designed to be capable of blocking translation movement of the closing surface 15, through the snapping the thumb wheel 21 over their fixed part in fully screwed condition.

Figure 6:
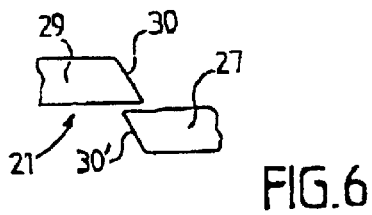
FIG. 6 illustrates a detail, identified by reference VI in preceding FIG. 4.

As illustrated in FIG. 6, body 23 of the thumb wheel 21 has, for this purpose a return member 29. The return member 29 is capable of snapping onto the indexing ring 27 with the help of inclined planes 30, 30' provided facing one another on the return member 29 and the indexing ring 27.

With further reference to FIGS. 2 and 4, it will be noted that the cartridge 10 includes, in its fixing portion 13, means 31 for holding the cartridge 10 in place. The means 31 promotes the axial prolongation 32 of the enclosure 15, the axial prolongation is capable of co-operating with the thicknesses of material 3, 3' to enable the cartridge 10 to be immobilised in the loading orifices 6, 6'.

The means 31 may be a threaded portion provided on the outer face of the enclosure 15. Alternatively, it may be a tapped portion provided opposite on a section 33 integral with the conduit 9 around the second port 6'.

The axial prolongation 32 of enclosure 15 can be provided, in the area of the outer end 19 of cartridge 10, with a protective ring 34 designed to locally conceal outer face 4 of fitting 1. The outer face 4 is thus protected from possible soiling caused by the introduction of the active compound.

The axial prolongation 32 of enclosure 15 can further have, at its end located at the outer end 19 side of cartridge 10, the indexing ring 27 (as shown in FIG. 5). Therefore, by rotating the thumb wheel 21, stops 25 of the thumb wheel 21 and 28 of the indexing ring 27 can co-operate with one another and enable the cartridge 10 to be screwed/unscrewed.

Fitting 1 can further include means 35 to ensure airtightness of the loading orifice 6, 6'. The means 35, preferably comprises a joint, co-operating on one hand, with a shoulder 36 provided in the area of the enclosure 15 and, on the other hand, with the walls of the thicknesses of material 3, 3' preferably with section 33.

The foregoing discussion discloses and describes a preferred embodiment of the invention. One skilled in the art will readily recognize from such discussion, and from the accompanying drawings and claims, that changes and modifications can be made to the invention without departing from the true spirit and fair scope of the invention as defined in the following claims.

What is claimed is:

1. A fitting for a motor vehicle, permitting a circulation of at least one stream of air, along a given path, behind at least one thickness of material defining a face of said fitting, said fitting inducing diffusing means for diffusing an active compound in said stream, characterized by the fact that said diffusing means are designed to be capable of being introduced, wholly or in part, through at least one loading orifice, or passing through said thicknesses of material from said outer face and emerging in said stream, said loading orifice being oriented transversely to the path of said stream, said diffusing means being also capable of being held in the area of said thickness or thicknesses of material, said diffusing means being located upstream of ventilation orifices provided on the front face of said fitting and in an area of which said at least one air stream emerges, said fitting further comprising an instrument panel capable of permitting the circulation of one of said air streams in the direction of each of its lateral ends, in the vicinity of which are located at least some of said ventilation orifices, said instrument panel being provided with the diffusing means in the area of one of its lateral faces, designed to be located opposite the front doors of the vehicle.

2. The fitting according to claim 1, wherein said diffusing means are removable, wholly or in part, in relation to the rest of said fitting.

3. The fitting according to claim 1, further comprising a panel defining said outer face and at least one flow conduit for said at least one air stream, provided behind said panel, said loading orifice being constituted by a first port, provided in said panel, and by a second port, provided in said conduit, in axial prolongation of one another.

4. The fitting according to claim 1, wherein said diffusing means comprise a cartridge extending in at least one direction, said cartridge being capable of being positioned, over a diffusing portion of its length in said direction, wherein so as to extend to meet the air stream, and over a fixing portion.

5. The fitting according to claim 4, in which said cartridge comprises diffusing portion, a support means for said active compound, designed to be volatile, and a permeable enclosure covering said support means.

6. The fitting according to claim 5, further including means for causing the permeability of said enclosure to vary.

7. The fitting according to claim 6, in which said enclosure has a surface for the passage of the vapours of said active compound, and said means for causing permeability to vary comprises a closing surface, wherein said closing surface is mobile between said support means and said enclosure, so as to adjust the aperture of said surface, wherein the movements of said closing surface are controlled from the end of the cartridge located in the area of said fixing portion.

8. The fitting according to claim 7, in which said enclosure and said closing surface comprises two coaxial cylinders, said closing surface being mobile in rotation about its longitudinal axis and having an axial prolongation along said fixing portion, said axial prolongation defining an outer end of said cartridge, wherein said closing surface is driven in rotation by adjusting a thumb wheel.

9. The fitting according to claim 8, wherein said cartridge is provided with indexing means permitting locating the relative positioning of said closing surface and said enclosure, wherein said indexing means comprise a mobile portion, provided in the area of said thumb wheel, and by a fixed portion of said fitting.

10. The fitting according to claim 9, wherein said closing surface, is in translation movement in relation to said enclosure along their common longitudinal axis, defines a housing to receive said support means, said indexing means being capable of blocking said translation movement of said indexing surface through the snapping of said thumb wheel over said fixed portion.

11. The fitting according to claim 5, wherein said cartridge includes, in its fixing portion, means for holding in place, an axial prolongation of said enclosure, said axial prolongation being capable of co-operating with said thicknesses of material to enable said cartridge be immobilised in said loading orifices.

12. The fitting according to claim 5, further comprising means to ensure air-tightness of said loading orifices co-operating, on one hand, with a shoulder in the area of said enclosure and, on the other hand, with the walls of said thicknesses of material.

13. An instrument panel for a motor vehicle comprising:

a panel member having generally opposed front and rear faces, said front face adapted to be oriented toward an interior of the motor vehicle, said panel member also defining a first thickness between said front and rear faces a ventilation duct adjacent to said rear face, said duct defining an opening and being coupled to at least one vent provided in said panel member adjacent to the opening;

a diffuser port extending through said panel member and said duct to define a second opening, the diffuser port terminating within said duct upstream of said at least one vent;

a diffuser cartridge removeably mounted in said diffuser port and extending Into said duct, said cartridge including a first housing having a plurality of first openings defined therein and a support media removeably positioned within said first housing and adapted to retain an active compound thereon to be diffused through said first openings into a stream of air passing through said duct.

14. The instrument panel of claim 13 wherein said cartridge is removeably mounted within said port.

15. The instrument panel of claim 13 wherein said cartridge includes a second housing positioned within said first housing, said second housing having a plurality of second openings defined therein, said second housing being moveable with regard to said first housing such that said second openings are variably aligned within said first openings, said support media being located within said second housing.

16. The instrument panel of claim 15 wherein said second housing is rotatable with regard to said first housing.

17. The instrument panel of claim 15 wherein said second housing is removeable from said first housing and said panel member.

18. The instrument panel of claim 17 wherein said support media is removeable from said second housing.

* * * * *

UNITED STATES PATENT AND TRADEMARK OFFICE
CERTIFICATE OF CORRECTION

PATENT NO. : 6,877,674 B2
DATED : April 12, 2005
INVENTOR(S) : Alain Choquet

It is certified that error appears in the above-identified patent and that said Letters Patent is hereby corrected as shown below:

Column 6,
Line 26, immediately after "faces" insert -- ; -- (semicolon).
Line 36, after "extending" delete "Into" and substitute -- into -- in its place.

Signed and Sealed this

Sixth Day of December, 2005

JON W. DUDAS
*Director of the United States Patent and Trademark Office*